(12) United States Patent
Sun et al.

(10) Patent No.: US 10,400,027 B2
(45) Date of Patent: Sep. 3, 2019

(54) PROTEIN AND USE THEREOF IN TREATING MULTIPLE SCLEROSIS

(71) Applicant: Shanghai Institutes for Biological Sciences, Chinese Academy of Sciences, Shanghai (CN)

(72) Inventors: Bing Sun, Shanghai (CN); Yuhan Zheng, Shanghai (CN); Pan Su, Shanghai (CN); Xiaodong Wu, Shanghai (CN)

(73) Assignee: Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 293 days.

(21) Appl. No.: 15/105,930

(22) PCT Filed: Dec. 19, 2014

(86) PCT No.: PCT/CN2014/094299
§ 371 (c)(1),
(2) Date: Jun. 17, 2016

(87) PCT Pub. No.: WO2015/090223
PCT Pub. Date: Jun. 25, 2015

(65) Prior Publication Data
US 2017/0022265 A1 Jan. 26, 2017

(30) Foreign Application Priority Data
Dec. 20, 2013 (CN) .......................... 2013 1 0713428

(51) Int. Cl.
*C07K 14/78* (2006.01)
*A61K 38/00* (2006.01)

(52) U.S. Cl.
CPC .............. *C07K 14/78* (2013.01); *A61K 38/00* (2013.01); *C07K 2319/30* (2013.01)

(58) Field of Classification Search
None
See application file for complete search history.

(56) References Cited

U.S. PATENT DOCUMENTS 5,872,234 A    2/1999  Bandman et al.
8,710,025 B2 * 4/2014  Wolfman .............. C07K 14/475
                                                        435/320.1

FOREIGN PATENT DOCUMENTS

| CN | 1652770   A | 8/2005  |
| CN | 101891814 A | 11/2010 |
| CN | 101899419 A | 12/2010 |
| CN | 102027013 A | 4/2011  |

OTHER PUBLICATIONS

Li, Z., et al. Nat. Immunol. 2011;12(2):178-186.*
Oyama et al., "Autoantibodies to extracellular matrix protein 1 in lichen sclerosus," Mechanisms of disease, Jul. 12, 2003, The Lancet, vol. 362, pp. 118-123.
Bing Sun, "Novel function of Extra-Cellular Matrix protein 1 (ECM1) in suppression of experimental autoimmune encephalomyelitus (EAE) by targeting Th17 cell differentiation and migration," Aug. 31, 2013, Abstracts of Symposium on immune cell biology across the Taiwan Strait, pp. 8-9.
Bhalerao, Jayant, Tylzanowksi, Przemko, Filie, Jane D, Kozak, Christine A. and Merregaert Joseph, "Molecular Cloning, Characterization, and Genetic Mapping of the cDNA Coding for a Novel Secretory Portein of Mouse", The Journal of Biological Chemistry, vol. 270, N0. 27, Jul. 7, 1995, pp. 16385-16394.
Chan, I., "The Role of Extracellular Matrix Protein 1 in Human Skin,", Clinical and Experimental Dermatology, vol. 29, 2004, pp. 52-56.
Clegg, Andrew and Bryant, Jackie, "Immunology drugs for Multiple Sclerosis: a Systematic Review of Clinical and Cost Effectiveness,",Exp. Opin. Pharmacother: (2001) 2 (4), pp. 623-639.
Compston, Alastair and Coles, Alasdair, "Multiple Sclerosis", Departemtn of Clinical Neurosciences, University of Cambridge Clinical School, Addenbrooke's Hospital, Cambridge, UK, Lancet 2008: 372; pp. 1501-1517, Oct. 25, 2008.
Dong, Xunhzhong, et al., "Research Progress of the Relationhship Between Extracellualr Matrix Protein-1 and Tumourigenesis", Journal of Clinical Hepatology, vol. 14, No. 3, pp. 230-232, Jun. 10, 2011 (Abstract in English).
Engelhardt, Britta, "Immune Cell Entry into the Central Nervous System: Involvement of Adhesion Molecules and Chemokines," Journal of the NEruological Sciences, 274: Jun. 24, 2008, pp. 23-26
Gasperini, Claudio and Ruggieri, Serena, "Development of oral agent in the treatment of multiple scelerosis: how the first available oral therapy, fingolimod will change therapeutic paradigm approach," Drug, Design and Therapy, Jul. 18, 2012, pp. 175-186.
Hamada, et al., "Lipoid Proteinosis Maps to 1q21 and is casued by Mutations in the Extracellular Matrix Protein 1 gene (ECM1)", Human Molesular Genetics, 2002, vol. 11 No. 7, pp. 833-840.
Mongiat, Maurizion, Fu, Jian, Oldershaw, Rachel, Greenhalgh, Robert, Gown, Allen M. and Iozzo, Renato V., "Perlecan Protein Core Interacts with Extracellular Matrix Protein 1 (EMC1), a Glycoprotein Involved in Bone Formation and Angiogenesis," The Journal of Biological Chemistry, vol. 278, No. 19, May 9, 2003, pp. 17491-17499.
Prendergast, Catriona T. and Anderston, Stephen M., "Immune Cell Entry to Central Nervous System—Current Understanding and Prospective Therapeutic Targets,", Endocrine, MEtabolic & Immune Disorders—Drug Targets, 2009, vol. 9, pp. 315-327.
Translation of International Search Report and Written Opinion from International Applicaton No. PCT/CN2014/094299 dated Apr. 13, 2015; 8 pages.
Smits, Patrick, Poumay, Yves, Karperien, Marcel, Tylzanowski, Prezemko, Wauters, Jan, Huylebroeck, Danny, Ponec, Maria and Merregaert, Jozef, "Differentiation—Dependent Alternative Spllicing and Expression of the Extracellular Matrix Protein 1 Gene in Human Keratinocytes," The Jouranl of Investigative Dermatology, vol. 114, No. 4, Apr. 2000, pp. 718-724.
NCBI Reference Sequence: NP_031925.2, extracellular matric protein 1 precursor[Mus musclus], Dec. 30, 2010. National Center for Biotechnology Information [database online]. Retrieved from https://www.ncbi.nlm.nih.gov/protein/170295832?sat=14&satkey=4816347. Accession No. NP_031925, Version: NP_031925.2, 3 pages.

* cited by examiner

*Primary Examiner* — G. R. Ewoldt
(74) *Attorney, Agent, or Firm* — Lee & Hayes, P.C.

(57) ABSTRACT

Provided are extracellular matrix protein 1 (ECM1) and fusion protein Fc-ECM1 of the ECM1 and the Fc sequence, and also provided are cloning construction and expression of the protein, and use of the protein in preparing a pharmaceutical composition for treating multiple sclerosis.

11 Claims, 5 Drawing Sheets
Specification includes a Sequence Listing.

SEQUENCE LISTING

<160> NUMBER OF SEQ ID NOS: 2

<210> SEQ ID NO 1
<211> LENGTH: 2436
<212> TYPE: DNA
<213> ORGANISM: Artificial sequence
<220> FEATURE:
<223> OTHER INFORMATION: Expression sequence of Fc-ECM1 fusion protein

<400> SEQUENCE: 1

```
atgctactag taaatcagtc acaccaaggc ttcaataagg aacacacaag caagatggta      60
agcgctattg ttttatatgt gcttttggcg gcggcggcgc attctgcctt tgcgggatcc     120
gcctctgagg gagccttcaa ggcttcagac cagcgagaga tgacgccaga gcgcctcttc     180
cagcacctcc atgaagtagg ttatgcagca ccccccttccc caccacaaac ccggagactc     240
cgagttgacc actctgtaac ttctctgcat gaccctcccc tctttgagga acaaagagaa     300
gtgcagcccc cttcctctcc agaagacatc cctgtgtacg aggaagactg gccccacttt     360
ctaaacccta atgtagataa agctggtcct gctgtccctc aagaagccat ccccctgcag     420
aaagagcagc cccctcccca agtccatatt gaacagaagg aaatagaccc gcctgcccag     480
cctcaggagg agattgtcca gaaagaggtg aagccacaca ccttggcggg ccagctccct     540
ccagagcccc ggacttggaa tccagcccgt cactgccagc agggacggag aggtgtctgg     600
ggccaccggc tggatggctt ccctcctgga cggccttctc cagacaatct gaagcagatc     660
tgccttcctg agcgtcagca tgtgatctac ggcccctgga acctgccgca gactggctac     720
tctcacctta gtcgccaggg agagaccctc aatgtgctgg agaccggata ctcccgctgc     780
tgtcgctgcc gcagcgacac aaaccgccta gactgtttga gcttgtgtg ggaggatgca     840 atgacccaat tttgtgaggc cgaattctct gtcaagaccc gcccccacct gtgctgcaga     900
ctgcgtgggg aggagcgatt ctcttgcttc cagaaggaag ctcctcgccc agactacctg     960
ctccgaccct gcccgtcca ccagaatggc atgtcctcag ggccccagtt gcctttcccc    1020
ccggggttgc ccacaccgga caatgtcaaa aacatctgtc tcctgagacg cttccgcgcc    1080
gtgccacgca acctccagc tactgacgcc atccagaggc agctgcaggc tctgactcgg    1140
ctggagacgg agttccagcg ctgctgccgc cagggccaca accacacttg cacatggaag    1200
gcctgggagg gtacccctgga tggatactgc gagcgggagc tggctataaa gacccacccc    1260
cactcgtgct gccactaccc tcctagtcct gcccgtgatg agtgcttcgc ccacctagct    1320
```

```
ccctatccca actatgaccg ggatatcttg acccttgacc tcagccgagt cacccccaac   1380
ctcatgggcc agctctgtgg aagtggaagg gtccttagca agcataaaca gattccgggg   1440
ctgatccaga atatgaccat ccgctgctgc gagcttccat atccagaaca ggcctgctgc   1500
ggcgaagagg agaaactggc cttcatcgag aacctctgtg gtccccggag gaattcgtgg   1560
aaagaccctg ccctctgctg tgacctgtct cctgaagata agcaaatcaa ctgcttcaat   1620
accaactacc tgaggaacgt ggctttagtg gctggagaca ctgggaatgc cactggcttg   1680
ggggagcagg gcccaactcg gggaacagat gccaaccccg cccctgggtc aaggaagaa    1740 ctcgagacat gccaccgtg cccagcacct gaactcctgg ggggaccgtc agtcttcctc   1800
ttccccccaa aacccaagga caccctcatg atctcccgga cccctgaggt cacatgcgtg   1860
gtggtggacg tgagccacga agaccctgag gtcaagttca actggtacgt ggacggcgtg   1920
gaggtgcata atgccaagac aaagccgcgg gaggagcagt acaacagcac gtaccgtgtg   1980
gtcagcgtcc tcaccgtcct gcaccaggac tggctgaatg gcaaggagta caagtgcaag   2040
gtctccaaca aagccctccc agcccccatc gagaaaacca tctccaaagc caaagggcag   2100
ccccgagaac cacaggtgta caccctgccc ccatcccggg atgagctgac caagaaccag   2160
gtcagcctga cctgcctggt caaaggcttc tatcccagcg acatcgccgt ggagtgggag   2220
agcaatgggc agccggagaa caactacaag accacgcctc ccgtgctgga ctccgacggc   2280
tccttcttcc tctacagcaa gctcaccgtg gacaagagca ggtggcagca ggggaacgtc   2340
ttctcatgct ccgtgatgca tgaggctctg cacaaccact acacgcagaa gagcctctcc   2400
ctgtctccgg gtaaaaagct tgtcgagaag tactag                            2436
```

<210> SEQ ID NO 2
<211> LENGTH: 811
<212> TYPE: PRT
<213> ORGANISM: Artificial sequence
<220> FEATURE:
<223> OTHER INFORMATION: Fc-ECM1 fusion protein

<400> SEQUENCE: 2

```
Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala Gly Ser Ala Ser Glu Gly Ala Phe Lys Ala
        35                  40                  45

Ser Asp Gln Arg Glu Met Thr Pro Glu Arg Leu Phe Gln His Leu His
    50                  55                  60

Glu Val Gly Tyr Ala Ala Pro Pro Ser Pro Gln Thr Arg Arg Leu
65                  70                  75                  80

Arg Val Asp His Ser Val Thr Ser Leu His Asp Pro Leu Phe Glu
                85                  90                  95

Glu Gln Arg Glu Val Gln Pro Pro Ser Ser Pro Glu Asp Ile Pro Val
            100                 105                 110

Tyr Glu Glu Asp Trp Pro Thr Phe Leu Asn Pro Asn Val Asp Lys Ala
        115                 120                 125

Gly Pro Ala Val Pro Gln Glu Ala Ile Pro Leu Gln Lys Glu Gln Pro
    130                 135                 140

Pro Pro Gln Val His Ile Glu Gln Lys Glu Ile Asp Pro Pro Ala Gln
145                 150                 155                 160
```

```
Pro Gln Glu Glu Ile Val Gln Lys Glu Val Lys Pro His Thr Leu Ala
            165                 170                 175
Gly Gln Leu Pro Pro Glu Pro Arg Thr Trp Asn Pro Ala Arg His Cys
        180                 185                 190
Gln Gln Gly Arg Arg Gly Val Trp Gly His Arg Leu Asp Gly Phe Pro
        195                 200                 205
Pro Gly Arg Pro Ser Pro Asp Asn Leu Lys Gln Ile Cys Leu Pro Glu
    210                 215                 220
Arg Gln His Val Ile Tyr Gly Pro Trp Asn Leu Pro Gln Thr Gly Tyr
225                 230                 235                 240
Ser His Leu Ser Arg Gln Gly Glu Thr Leu Asn Val Leu Glu Thr Gly
                245                 250                 255
Tyr Ser Arg Cys Cys Arg Cys Arg Ser Asp Thr Asn Arg Leu Asp Cys
            260                 265                 270
Leu Lys Leu Val Trp Glu Asp Ala Met Thr Gln Phe Cys Glu Ala Glu
        275                 280                 285
Phe Ser Val Lys Thr Arg Pro His Leu Cys Cys Arg Leu Arg Gly Glu
        290                 295                 300
Glu Arg Phe Ser Cys Phe Gln Lys Glu Ala Pro Arg Pro Asp Tyr Leu
305                 310                 315                 320
Leu Arg Pro Cys Pro Val His Gln Asn Gly Met Ser Ser Gly Pro Gln
            325                 330                 335
Leu Pro Phe Pro Pro Gly Leu Pro Thr Pro Asp Asn Val Lys Asn Ile
        340                 345                 350
Cys Leu Leu Arg Arg Phe Arg Ala Val Pro Arg Asn Leu Pro Ala Thr
        355                 360                 365
Asp Ala Ile Gln Arg Gln Leu Gln Ala Leu Thr Arg Leu Glu Thr Glu
    370                 375                 380
Phe Gln Arg Cys Cys Arg Gln Gly His Asn His Thr Cys Thr Trp Lys
385                 390                 395                 400
Ala Trp Glu Gly Thr Leu Asp Gly Tyr Cys Glu Arg Glu Leu Ala Ile
                405                 410                 415
Lys Thr His Pro His Ser Cys Cys His Tyr Pro Pro Ser Pro Ala Arg
            420                 425                 430
Asp Glu Cys Phe Ala His Leu Ala Pro Tyr Pro Asn Tyr Asp Arg Asp
        435                 440                 445
Ile Leu Thr Leu Asp Leu Ser Arg Val Thr Pro Asn Leu Met Gly Gln
    450                 455                 460
Leu Cys Gly Ser Gly Arg Val Leu Ser Lys His Lys Gln Ile Pro Gly
465                 470                 475                 480
Leu Ile Gln Asn Met Thr Ile Arg Cys Cys Glu Leu Pro Tyr Pro Glu
                485                 490                 495
Gln Ala Cys Cys Gly Glu Glu Lys Leu Ala Phe Ile Glu Asn Leu
            500                 505                 510
Cys Gly Pro Arg Arg Asn Ser Trp Lys Asp Pro Ala Leu Cys Cys Asp
        515                 520                 525
Leu Ser Pro Glu Asp Lys Gln Ile Asn Cys Phe Asn Thr Asn Tyr Leu
    530                 535                 540
Arg Asn Val Ala Leu Val Ala Gly Asp Thr Gly Asn Ala Thr Gly Leu
545                 550                 555                 560
Gly Glu Gln Gly Pro Thr Arg Gly Thr Asp Ala Asn Pro Ala Pro Gly
                565                 570                 575
```

-continued

```
Ser Lys Glu Glu Leu Glu Thr Cys Pro Pro Cys Pro Ala Pro Glu Leu
            580                 585             590

Leu Gly Gly Pro Ser Val Pro Leu Phe Pro Pro Lys Pro Lys Asp Thr
        595             600                 605

Leu Met Ile Ser Arg Thr Pro Glu Val Thr Cys Val Val Val Asp Val
    610             615             620

Ser His Glu Asp Pro Glu Val Lys Phe Asn Trp Tyr Val Asp Gly Val
625             630             635                     640

Glu Val His Asn Ala Lys Thr Lys Pro Arg Glu Glu Gln Tyr Asn Ser
            645             650                 655

Thr Tyr Arg Val Val Ser Val Leu Thr Val Leu His Gln Asp Trp Leu
        660             665             670

Asn Gly Lys Glu Tyr Lys Cys Lys Val Ser Asn Lys Ala Leu Pro Ala
        675             680             685

Pro Ile Glu Lys Thr Ile Ser Lys Ala Lys Gly Gln Pro Arg Glu Pro
    690             695             700

Gln Val Tyr Thr Leu Pro Pro Ser Arg Asp Glu Leu Thr Lys Asn Gln
705             710             715                     720

Val Ser Leu Thr Cys Leu Val Lys Gly Phe Tyr Pro Ser Asp Ile Ala
            725             730             735

Val Glu Trp Glu Ser Asn Gly Gln Pro Glu Asn Asn Tyr Lys Thr Thr
            740             745             750

Pro Pro Val Leu Asp Ser Asp Gly Ser Phe Phe Leu Tyr Ser Lys Leu
        755             760             765

Thr Val Asp Lys Ser Arg Trp Gln Gln Gly Asn Val Phe Ser Cys Ser
    770             775             780

Val Met His Glu Ala Leu His Asn His Tyr Thr Gln Lys Ser Leu Ser
785             790             795                     800

Leu Ser Pro Gly Lys Lys Leu Val Glu Lys Tyr
            805             810
```

PROTEIN AND USE THEREOF IN TREATING MULTIPLE SCLEROSIS

CROSS REFERENCE TO RELATED PATENT APPLICATION

This application is a national phase application of International Application No. PCT/CN2014/094299, filed on Dec. 19, 2014, entitled "Protein and Use Thereof in Treating Multiple Sclerosis", and claims foreign priority to Chinese Patent Application No. 201310713428.6 filed on Dec. 20, 2013, entitled "Fusion Protein and Use Thereof in Treating Multiple Sclerosis", which applications are hereby incorporated by reference in their entirety.

FIELD OF THE INVENTION

The invention belongs to the field of biomedicine, in particular, relates to cloning and expression of a protein and to medical application thereof. This aspect also relates to use of extracellular matrix protein1 and its fusion protein in treating multiple sclerosis.

BACKGROUND OF THE INVENTION

Multiple Sclerosis and Pathology Thereof

Multiple sclerosis (MS) is a chronic autoimmune disease common in central nervous system (CNS), the main changes of lesion are early cerebral white matter demyelination and axon loss as, causing various symptoms, including sensory alteration, visual impairment, muscle weakness, melancholy, coordination and speech difficulties, severe fatigue, cognitive disorder, disequilibrium, body heat and pain, etc., which can cause motion disorder and disability in severe case.

MS mostly involves young and middle-aged people, having very high disability rate. Epidemiologic studies suggest that about 2.5 million people suffer from multiple sclerosis around the world; prevalence rate is between 2 and 150 people per 100,000 people according to different countries or particular ethnic groups. Symptoms of 80% MS patients belong to relapsing-remitting (RR), manifested by multiple relapses and remissions, with stable disease during two recurrence periods, as disease symptoms progressively deteriorate, after 10-20 years, about half of RRMS patients will turn into secondary progressive (SP). The remaining 20% MS patients belong to primary progressive (PP), manifested by no remission after the onset of illness, presenting progressive deterioration.

A lot of studies show that various immune cells are involved in pathogenesis of MS, including T cell, B cell and macrophage, etc. Experimental autoimmune encephalomyelitis (EAE) is an organ specific autoimmune disease, occurring in central nervous system, a delayed allergic disease which is induced by active immunity of myelin protein antigens on experimental animals and has chronic, repeated attacking, CNS inflammatory demyelinating characteristics, main pathological features are perivascular inflammatory cell infiltration and myelin sheath response. Mouse EAE (experimental autoimmune encephalomyelitis) model has the same characteristics as human MS in clinical symptom, biochemical index, immunity and pathology and other aspects, thus it is a currently international generally recognized ideal animal model for studying MS (Chinese Journal of Cell Biology, Vol 34, pp. 826-836).

Under normal physiological conditions, under the control of blood-brain barrier (BBB), only a small number of immune cells may enter central nervous system to play a role in immunosurveillance. However, in virus/bacterial infection or inflammatory conditions, a lot of peripheral immune cells may pass blood-brain barrier and enter central nervous system CNS. Inflammatory $CD4^+$ T cells invade CNS, activate microglia cells and recruit inflammatory macrophages to enter CNS, finally leading to destroy of CNS myelin and cell death of oligodendrocytes, which is the pathogenesis of EAE. EAE and multiple sclerosis can be effectively treated and alleviated by inhibiting inflammatory $CD4^+$ T cell migration, preventing it from entering central nervous system. In 2010, the first oral drug FTY720/Gilenya for treating multiple sclerosis was developed by Novartis, the mechanism of which was relieving symptoms of multiple sclerosis by inhibiting inflammatory $CD4^+$ T cell migration.

Existing Drugs and Shortcomings Thereof

The pathogenesis of MS is complex and not entirely clear yet, there is no special effective drug for treating MS. Since significant inflammatory changes exist in acute MS damage, MS treatment has been focusing on anti-inflammation in the past 30 years.

Now there have been 7 drugs approved for treating MS patients, including glatiramer acetate (GA), recombinant interferon β, natalizumab, mitoxantrone, etc. These drugs are respectively suitable for MS with different symptoms, and can reasonably alleviate recurrent multiple sclerosis, reduce disease relapse in part of patients or reduce clinical symptoms. Meanwhile, these drugs have some side effects. For example, a common adverse effect of recombinant interferon β is an influenza-like symptom, continuing for 24-48 h which usually diminishes after 2-3 months. IFN-β1a may cause swelling and pain in injection sites, liver function impairment and severe allergic reaction, etc., IFN-β1b may cause swelling and tenderness in injection sites, occasionally causing local necrosis, slightly increased serum transaminase, leucopenia or anemia. Natalizumab may cause progressive multifocal leukoencephalopathy (PML). Common side effects of mitoxantrone include nausea, baldness, leucopenia, anemia and cardiotoxicity, etc. Therefore, there is the need of great significance to develop new diagnosis and therapeutic approaches directed at the pathogenesis of MS, as well as new effective therapeutic drugs for MS with reduced side effects.

Extracellular Matrix Protein 1

Extracellular matrix protein 1 (ECM1) was found in 1994 as a 85KD glycosylated protein secreted by stromal osteoblast cell line MN7. Researchers have found the human homologous gene of ECM1 in human chromosome 1q21 position in 1997. Later, researches showed that ECM1 played an important regulatory role in cartilagenous osteogenesis, endothelial proliferation and angiogenesis. Since 2002, researchers have found that ECM1 mutations cause lipoid proteinosis and can produce spontaneous ECM1 antibodies in patients suffering from lichen sclerosus, leading to loss of ECM1 function and diseases etc. This indicates the important function of ECM1 gene, which has also been the main direction of ECM1 study in the recent years. However, wild type ECM1 is low in expression level, difficult to purify, and prone to structural changes during purification process, which finally causes activity loss. Uptill now, function of ECM1 in immune system disease has been rarely reported.

SUMMARY OF THE INVENTION

Confronted with the above-mentioned problems found with the wild type ECM1, the inventors constructed a fusion protein named Fc-ECM1, which can be used for engineered expression and function study of ECM1. The inventors studied and proved that the protein and the fusion protein obtained from the engineered expression are useful in treating multiple sclerosis.

The inventors have discovered that the protein obtained from fusing ECM1 protein and the Fc sequence in IgG is easier to purify by means of affinity chromatography, and can obtain an appropriate protein glycosylation modification in host, whereby to maintain the activity and function of the wild type protein in the expressed protein. In a later stage of the induced EAE model in mouse, treating with Fc-ECM1 protein significantly relieves the disease in seveity, as reflected by a lowered disease score, as demonstrated by decrease in number of inflammatory cell infiltrating the central nervous system and decreased pathological damage. Further studies show that Fc-ECM1 inhibits pathogenic Th cell migration toward CNS. Existing drugs for MS are mostly synthetic, which have various side effects. In contrast, ECM1 is specifically high-expressed by Th2 cell, and is a naturally existing protein having the structure and composition commonly seen in human of physiological homostasis. It is thus expected that it has less side effects to human. The studies on ECM1 and Fc-ECM1 provide new theoretical basis for EAE models and pathogenic mechanism as well as treatment of human multiple sclerosis. These proteins have potential value for further development of drugs for treating multiple sclerosis.

One major object of the present invention is to provide an Fc-ECM1 fusion protein which can be effectively produced by engineered expression, be easily purified and maintain the normal function and activity of ECM1.

In an embodiment, the present invention provides a fusion protein named "Fc-ECM1" comprising an extracellular matrix protein 1 (ECM1) fused to an Fc sequence of human IgG. Particularly, in the fusion protein of the present invention, the amino acid sequence of said extracellular matrix protein 1 is as set forth by the amino acids 41-580 in SEQ ID NO.: 2, the amino acid sequence of said Fc sequence is as set forth by the amino acids 583-811 in SEQ ID NO.: 2. In a particular embodiment, the sequence of said fusion protein is as set forth by amino acids 41-811 in SEQ ID NO.: 2.

In another embodiment, the present invention provides a nucleic acid comprising an encoding sequence of the Fc-ECM1. Particularly, said nucleic acid molecule comprises a nucleotide sequence encoding an extracellular matrix protein 1, such as but not limited to the sequence of nucleotides 121-1740 in SEQ ID NO.: 1, and a nucleotide sequence encoding said Fc sequence, such as but not limited to the sequence of nucleotides 1747-2433 in SEQ ID NO.: 1. Optionally, said nucleic acid further contains a nucleotide sequence encoding a signal peptide, for example, a nucleotide sequence encoding an insect signal peptide, like one of the amino acid sequence of residues 2-40 in SEQ ID NO.: 2, wherein the nucleotide sequence can be but is not limited to the sequence of nucleotides 4-120 in SEQ ID NO.: 1. In a particular embodiment, the sequence of said nucleic acid is as set forth by nucleotides 1-2436, 4-2436, 1-2433, 4-2433, 121-2436 or 121-2433 in SEQ ID NO.: 1.

In another embodiment, the present invention provides an expression vector for expressing an Fc-ECM1 fusion protein. In a particular embodiment, said expression vector comprises a nucleic acid encoding an Fc-ECM1 fusion protein. In another embodiment, the present invention provides a host cell expressing an Fc-ECM1 fusion protein. In a particular embodiment, said host cell is a eukaryotic expression system in insect cell, e.g., an insect-baculovirus expression system.

One major object of the present invention is to provide a pharmaceutical composition for treating multiple sclerosis. In an embodiment, said pharmaceutical composition comprises (A) a therapeutically effective amount of an extracellular matrix protein 1; and (B) a pharmaceutically or immunologically acceptable carrier or excipient. In a particular embodiment, the pharmaceutical composition comprises 0.001-99.9 wt % of the extracellular matrix protein 1, based on the total weight of the pharmaceutical composition. In a preferred embodiment, said pharmaceutical composition comprises 1-95 wt %, preferably 5-90 wt %, more preferably 10-80 wt % of the extracellular matrix protein 1, based on the total weight of the pharmaceutical composition. In a particular embodiment, said carriers include but are not limited to water, aqueous buffers, ethanol, polyols, vegetable oil, injectable organic esters, and mixtures thereof. Particularly, said aqueous buffer includes but not limited to the group consisting of phosphate buffer, Tris buffer, borate buffer, succinate buffer, histidine buffer and citrate buffer.

Another object of the present invention is to provide a method for treating multiple sclerosis, which comprises administering a therapeutically effective amount of an extracellular matrix protein 1 or the fusion protein Fc-ECM1 to a subject in need of the treatment or alleviation. Said protein may be administered in the form of a pharmaceutical composition. Said subject may be a mammal, for example, a human. Said method can treat or alleviate multiple sclerosis by inhibiting T cell migration.

Another object of the present invention is to provide a use of extracellular matrix protein 1 in drug preparation, wherein the drug is used for treating or alleviate multiple sclerosis.

In some embodiments, the pharmaceutical composition and the method according to the present invention are capable of effectively treating multiple sclerosis or alleviating its symptoms, wherein said symptoms include but are not limited to: sensory alteration, visual impairment, muscle weakness, melancholy, coordination and speech difficulties, severe fatigue, cognitive disorder, disequilibrium, body heat, pain, motion disorder, disability, etc.

In some embodiments, in the pharmaceutical composition or the method according to the present invention, said extracellular matrix protein 1 or the fusion protein thereof may be mixed with an aqueous or non-aqueous vector for administering or for preparing pharmaceutical compositions. Pharmaceutically acceptable carriers for therapeutic use are well known in the field. Carriers include but are not limited to: water, aqueous buffers, ethanol, polyols (e.g., glycerol, propanediol, polyethylene glycol, etc.), and suitable mixtures thereof, vegetable oil, such as olive oil, and injectable organic esters, such as ethyl oleate, etc. Aqueous buffers include but are not limited to: phosphate buffer, Tris buffer, borate buffer, succinate buffer, histidine buffer, citrate buffer, etc.

In some embodiments, the extracellular matrix protein 1 according to the present invention may be administered through oral administration, injection, local administration or other known techniques. By "injection", it includes but is not limited to: subcutaneous injection, intravenous injection, intraperitoneal, intramuscular injection, intrasternal injection and infusion. An effective amount of an extracellular matrix protein 1 may be administered to a subject by a single dosing or multiple dosings, like once a day, once every other day, once every three days, twice a week, once a week, twice a month, once a month, etc. In certain embodiments, the administration dosage of said extracellular matrix protein 1 is about 60 mg/kg to 0.025 mg/kg, preferably about 0.025 mg/kg-15 mg/kg, such as 4 mg/kg or 5 mg/kg. One skilled in the art can determine the exact dosage and formulation using known techniques according to the specific therapeutic purpose and therapeutic effect as desired, see, e.g., *Remington: The Science and Practice of Pharmacy*, Gennaro ed. (2003, 20<sup>th</sup> version) and Pickar, *Dosage Calculations* (1999), etc.

The present invention also relates to use of the extracellular matrix protein 1 and the fusion protein Fc-ECM1 as well as the pharmaceutical composition in treating or alleviating multiple sclerosis. Another aspect of the present invention relates to a method for treating or alleviating multiple sclerosis in a mammal subject, wherein the method comprises administering a therapeutically effective amount of an extracellular matrix protein 1 or fusion protein Fc-ECM1 or a pharmaceutical composition comprising same to said subject.

Based on the disclosure herein, other aspects of the present invention would be obvious to those skilled in the art.

DESCRIPTION OF THE DRAWINGS

In each figure, the error bar represents a standard error, *: $p<0.05$, : $p<0.01$, *: $p<0.001$.

DESCRIPTION OF EMBODIMENTS

The effects, effectiveness and action mechanism of the Fc-ECM1 according to the present invention in treating multiple sclerosis are demonstrated and validated as specified below using a relevant mouse model. The experiments and evaluations are provided merely for exemplifying and explaining the present invention, rather than to limit the scope of the present invention. Experiments are carried out according to the conventional or standard procedures or according to the manufacturer's instruction, unless otherwise specified.

I. Materials and Methods

Materials

The reagents used were all purchased Sigma, unless otherwise specified, and the reagents, materials, apparatus and equipments used in the examples are all of medical grade.

Animals: C57BL/6 mice purchased from Shanghai Laboratory Animal Center, CAS, housed (SPF grade) in laboratory animal center of Shanghai Institute of Biochemistry and Cell Biology, CAS; Transgenic mice (Fc-ECM1$^{Tg}$) purchased from laboratory animal center of Shanghai Research Center of the Southern model organisms, which comprises ECM1 gene cloned downstream to human CD2 promoter for specific high expression in T cells.

Cell line: A549 cells obtained from Shanghai Institute of Biochemistry and Cell Biology, CAS, culture and passage are performed in high glucose DMEM+10% FBS under conventional conditions.

Reagents: pertussis toxin (PTX) from *Bordetella pertussis*, Freund's Adjuvant, Complete, Solvent Blue 38 and Percoll purchased from Sigma; DMEM, RPMI 1640 media and fetal calf serum purchased from Gibco BRL; Transfection agent Lipofectamine, a product of Invitrogen; Human IgG purchased from Shanghai Linc-Bio Science Co. LTD; Small-molecule inhibitor GM6001 purchased from Millipore, which blocks immune cells from crossing the blood-brain barrier basal lamina. MOG$_{35-55}$: MEVGWYR-SPFSRVVHLYRNGK, synthesized by CHINAPEPTIDE.

Cytokines and Antibodies

For T cell culture in vitro: recombinant mouse IL-12, IL-23 and human IL-2 purchased from R&D, recombinant mouse IL-1α, IL-6 and human TGF-β1 purchased from Peprotech; Anti-mouse CD3 (145-2C11), anti-CD28 (37.51), anti-mouse IL-4 (11B11) purchased from BD Pharmingen, anti-mouse IFN-γ (XMG1.2) purchased from eBioscience. Mouse CD4 antibody used in cell-sorting was purchased from Miltenyi Biotec.

For the flow cytometry experiment: FITC anti-mouse IFN-γ (XMG1.2) purchased from eBioscience, FITC anti-mouse CD4 (GK1.5), PerCP anti-mouse CD4 (RM4-5), PE anti-mouse IL-17 (TC11-18H10) obtained from BD Pharmingen.

For the Western blot: HA murine monoclonal antibody (16B2), a product of Covance, Cat.#CO-MMS-101R; ECM1 polyclonal antibody was prepared by our lab (Specifically, we expressed prokaryotic proteins respectively containing a 258-amino acid-fragment corresponding to residues 1024-1798 of the mouse ECM1 gene mRNA and a 282-amino acid-fragment corresponding to residues 178-1024 of the mouse ECM1 mRNA; Rabbit was immunized with the prokaryotic proteins to obtain polyclonal antibodies against the N-terminal and the C-terminal); HRP-labelled anti-rabbit IgG secondary antibody, a product of Southern Biotechnology Associates, Cat.#4050-05; HRP-labelled anti-mouse IgG secondary antibody, a product of R&D, Cat.#HAF007.

EAE Induction and Scoring

Pre-Experiment Preparation

A. Preparation of complete Freund's adjuvant (CFA): adding heat-inactivated *Mycobacterium tuberculosis* (TB) to incomplete Freund's adjuvant (IFA) to the final concentration of 5 mg/ml, thoroughly mixing before use.

B. Emulsification of antigen: two glass syrings were connected by a T-branch pipe, PBS: CFA and antigen MOG (20 mg/ml) were added to the two syrings (300 μs MOG, 85 μl PBS and 100 μl CFA per 200 μl emulsion), respectively; after removing bubbles, the contents were thoroughly mixed and emulsified by repeated suction-and-blow for about 500 times. C57BL/6 mice were immunized with the fragment peptide $MOG_{35-55}$ as the antigen. $MOG_{35-55}$ is strongly encephalitogenic, and can produce significant T cell immune response, and is the most widely used antigen peptide in induced EAE models in C57BL/6 mice.

Establishment of EAE Model and Administration

A. 6-8 week-old C57BL/6 female mice, weighed about 25 g, were used in the experiment. On the day of immunization (day 0), each mouse received antigen injection, 200 µl well-emulsified antigen was subcutaneously injected at three points: posterior thigh root, 50 µl each side, 100 µl tail root; meanwhile, pertussis toxin (PTX) 300 ng/mouse (dissolved in 100 µl PBS) was administered by intraperitoneal injection.

B. On day 2, each mouse was administered with an additional does of 300 ng PTX by intraperitoneal injection (the same concentration as above).

C. Treatment: On day 8, day 11 and day 14 of the immunization, Fc-ECM1 fusion protein (100 µs/mouse, dissolved in 200 µl PBS) was administered to mice in the treatment group by caudal vein injection, an identical volume of human IgG protein as the control (100 µg/mouse, dissolved in 200 µl PBS) was administered to mice in the control group.

EAE Clinical Scoring Criteria

Since the day of immunization, the mice are observed on clinical performance, EAE disease status was scored, as appropriate for the experiment and the scores were recorded for 20 to 60 days, generally about 30 days, or until the mice die. The scoring criteria are as follows, Score 0: no abnormality;
Score 1: tail paralysis;
Score 2: posterior limb fatigue, weakness, claudication;
Score 3: posterior limb complete paralysis;
Score 4: paralysis of both posterior limbs and anterior limb fatigue;
Score 5: death.

Pathological Tissue Slice and Staining

Paraffin Embedding of Mouse Spinal Cord Tissue

A. Tissue collection and fixation: mouse spinal cord samples were harvested at peak of EAE. Details were as follows: mice were anesthetized on day 24 after the EAE immunization, after 4% paraformaldehyde perfusion, mouse spinal cord samples were isolated, and then fixed at room temperature (RT) by 4% paraformaldehyde for 2-3 days.

B. Gradient dehydration and transparentizing: the fixed spinal cord samples was sequential placed in 50%, 70%, 80%, 95% and 100% ethanol solutions in the specified order, each for 1 h, to dehydrate. Then, put the spinal cord in a solution of ethanol: xylene at the ratio of 1:1 of for 1 h, take it out, and then put it in xylene for 5-10 min, until the tissue was close to transparent. Immerse it in paraffin at 60° C. overnight.

C. Embedding: Cut the spinal cord into small pieces of about 0.3 cm, followed by paraffin embedding according to standartd procedure; store it at −20° C. before use.

HE Staining

The paraffin sections stored at −20° C. were taken out, dried at 37° C., prepared by dewaxing, rehydration, hematoxylin staining, eosin staining, dehydrating to transparent, and mounting according to standard procedures, and then dired for storage before use.

Fast Blue Staining

The paraffin sections stored at −20° C. were taken out, dried at 37° C., placed in 0.1% FastBlue solution at 60° C. overnight, and the floating was washed out by clear water. Differentiation was repeated until it was observed under microscope that the peripheral white matter in spinal core appears blue while the internal gray matter was colourless. The specimen was then prepared by eosin staining, crystal violet staining, dehydration and clearing, after mounting, and then dried for storage before use.

Preparation of Fc-ECM1 Fusion Protein

To obtain the Fc-ECM1 fusion protein having biological activity, a eukaryotic expression system in insect cell (Bac-to-Bac Baculovirus Expression Systems, purchased from Invitrogen) was used, and the gene encoding ECM1 was used to construct the nucleotide sequence as set forth by SEQ ID NO.: 1, to express the ECM1 protein fused to human IgG Fc fragment (i.e., fusion protein Fc-ECM1, with the amino acid sequence as set forth by SEQ ID NO.: 2).

SEQ ID NO.: 1 (encoding nucleotide sequence for Fc-ECM1 protein):
ATGCTACTAGTAAATCAGTCACACCAAGGCTTCAATAAGGAACACACA

AGCAAGATGGTAAGCGCTATTGTTTTATATGTGCTTTTGGCGGCGGCG

GCGCATTCTGCCTTTGCGGGATCCGCCTCTGAGGGAGCCTTCAAGGCT

TCAGACCAGCGAGAGATGACGCCAGAGCGCCTCTTCCAGCACCTCCAT

GAAGTAGGTTATGCAGCACCCCCTTCCCCACCACAAACCCGGAGACTC

CGAGTTGACCACTCTGTAACTTCTCTGCATGACCCTCCCCTCTTTGAG

GAACAAAGAGAAGTGCAGCCCCCTTCCTCTCCAGAAGACATCCCTGTG

TACGAGGAAGACTGGCCCACTTTCCTAAACCCTAATGTAGATAAAGCT

GGTCCTGCTGTCCCTCAAGAAGCCATCCCCCTGCAGAAAGAGCAGCCC

CCTCCCCAAGTCCATATTGAACAGAAGGAAATAGACCCGCCTGCCCAG

CCTCAGGAGGAGATTGTCCAGAAAGAGGTGAAGCCACACACCTTGGCG

GGCCAGCTCCCTCCAGAGCCCGGACTTGGAATCCAGCCCGTCACTGC

CAGCAGGGACGGAGAGGTGTCTGGGGCCACCGGCTGGATGGCTTCCCT

CCTGGACGGCCTTCTCCAGACAATCTGAAGCAGATCTGCCTTCCTGAG

CGTCAGCATGTGATCTACGGCCCCTGGAACCTGCCGCAGACTGGCTAC

TCTCACCTTAGTCGCCAGGGAGAGACCCTCAATGTGCTGGAGACCGGA

TACTCCCGCTGCTGTCGCTGCCGCAGCGACACAAACCGCCTAGACTGT

TTGAAGCTTGTGTGGGAGGATGCAATGACCCAATTTTGTGAGGCCGAA

TTCTCTGTCAAGACCCGCCCCCACCTGTGCTGCAGACTGCGTGGGGAG

GAGCGATTCTCTTGCTTCCAGAAGGAAGCTCCTCGCCCAGACTACCTG

CTCCGACCCTGCCCCGTCCACCAGAATGGCATGTCCTCAGGGCCCCAG

TTGCCTTTCCCCCGGGGTTGCCCACACCGGACAATGTCAAAAACATC

TGTCTCCTGAGACGCTTCCGCGCCGTGCCACGCAACCTCCCAGCTACT

GACGCCATCCAGAGGCAGCTGCAGGCTCTGACTCGGCTGGAGACGGAG

TTCCAGCGCTGCTGCCGCCAGGGCCACAACCACACTTGCACATGGAAG

GCCTGGGAGGGTACCCTGGATGGATACTGCGAGCGGGAGCTGGCTATA

AAGACCCACCCCCACTCGTGCTGCCACTACCCTCCTAGTCCTGCCCGT

GATGAGTGCTTCGCCCACCTAGCTCCCTATCCCAACTATGACCGGGAT

ATCTTGACCCTTGACCTCAGCCGAGTCACCCCCAACCTCATGGGCCAG

CTCTGTGGAAGTGGAAGGGTCCTTAGCAAGCATAAACAGATTCCGGGG

-continued
```
CTGATCCAGAATATGACCATCCGCTGCTGCGAGCTTCCATATCCAGAA

CAGGCCTGCTGCGGCGAAGAGGAGAAACTGGCCTTCATCGAGAACCTC

TGTGGTCCCCGGAGGAATTCGTGGAAAGACCCTGCCCTCTGCTGTGAC

CTGTCTCCTGAAGATAAGCAAATCAACTGCTTCAATACCAACTACCTG

AGGAACGTGGCTTTAGTGGCTGGAGACACTGGGAATGCCACTGGCTTG

GGGGAGCAGGGCCCAACTCGGGGAACAGATGCCAACCCCGCCCCTGGG

TCCAAGGAAGAActcgagACATGCCCACCGTGCCCAGCACCTGAACTC

CTGGGGGGACCGTCAGTCTTCCTCTTCCCCCCAAAACCCAAGGACACC

CTCATGATCTCCCGGACCCCTGAGGTCACATGCGTGGTGGTGGACGTG

AGCCACGAAGACCCTGAGGTCAAGTTCAACTGGTACGTGGACGGCGTG

GAGGTGCATAATGCCAAGACAAAGCCGCGGGAGGAGCAGTACAACAGC

ACGTACCGTGTGGTCAGCGTCCTCACCGTCCTGCACCAGGACTGGCTG

AATGGCAAGGAGTACAAGTGCAAGGTCTCCAACAAAGCCCTCCCAGCC

CCCATCGAGAAAACCATCTCCAAAGCCAAAGGGCAGCCCCGAGAACCA

CAGGTGTACACCCTGCCCCCATCCCGGGATGAGCTGACCAAGAACCAG

GTCAGCCTGACCTGCCTGGTCAAAGGCTTCTATCCCAGCGACATCGCC

GTGGAGTGGGAGAGCAATGGGCAGCCGGAGAACAACTACAAGACCACG

CCTCCCGTGCTGGACTCCGACGGCTCCTTCTTCCTCTACAGCAAGCTC

ACCGTGGACAAGAGCAGGTGGCAGCAGGGGAACGTCTTCTCATGCTCC

GTGATGCATGAGGCTCTGCACAACCACTACACGCAGAAGAGCCTCTCC

CTGTCTCCGGGTAAAAAGCTTGTCGAGAAGTACTAG
```

Therein, the first three nucleotides are start codon and the last three nucleotides are stop codon; the sequence in bold encodes an insect signal peptide sequence; the sequence underlined encodes Fc-tag, the "ctcgag" in bold and lowercase is an artificially introduced enzyme cleavage site, and the remaining encodes the ECM1 protein.

SEQ ID NO.: 2 (the amino acid sequence of Fc-ECM1 with a signal peptide):
MLLVNQSHQGFNKEHTSKMVSAIVLYVLLAAAAHSAFAGSASEGAFKAS

DQREMTPERLFQHLHEVGYAAPPSPPQTRRLRVDHSVTSLHDPPLFEEQ

REVQPPSSPEDIPVYEEDWPTFLNPNVDKAGPAVPQEAIPLQKEQPPPQ

VHIEQKEIDPPAQPQEEIVQKEVKPHTLAGQLPPEPRTWNPARHCQQGR

RGVWGHRLDGFPPGRPSPDNLKQICLPERQHVIYGPWNLPQTGYSHLSR

QGETLNVLETGYSRCCRCRSDTNRLDCLKLVWEDAMTQFCEAEFSVKTR

PHLCCRLRGEERFSCFQKEAPRPDYLLRPCPVHQNGMSSGPQLPFPPGL

PTPDNVKNICLLRRFRAVPRNLPATDAIQRQLQALTRLETEFQRCCRQG

HNHTCTWKAWEGTLDGYCERELAIKTHPHSCCHYPPSPARDECFAHLAP

YPNYDRDILTLDLSRVTPNLMGQLCGSGRVLSKHKQIPGLIQNMTIRCC

ELPYPEQACCGEEEKLAFIENLCGPRRNSWKDPALCCDLSPEDKQINCF

NTNYLRNVALVAGDTGNATGLGEQGPTRGTDANPAPGSKEEleTCPPCP

APELLGGPSVPLFPPKPKDTLMISRTPEVTCVVVDVSHEDPEVKFNWYV

DGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDI

AVEWESNGQPENNYKTTPPVLDSDGSFFLYSKLTVDKSRWQQGNVFSCS

VMHEALHNHYTQKSLSLSPGKKLVEKY

Therein, the part in bold is the insect signal peptide with a methionine encoded by the start codon, the underlined part is the amino acid sequence of Fc-tag, the "le" in bold and lowercase is the amino acid encoded by the artificial enzyme cleavage site, and the remaining is the amino acid sequence of the ECM1 protein.

Figure 1:
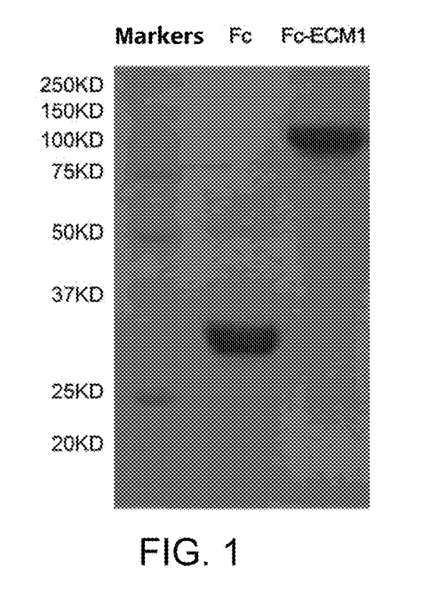
FIG. 1 shows a Coomassie brilliant blue staining of the purified protein.

Basically, the procedure was as follows: clone the encoding sequence as set forth by SEQ ID NO.: 2 into the vector pFastBac™, screen for the correctly recombined Bacmid DNA, transfect the adherent insect cell line HighFive with the Bacmid using CellFECTIN, use the obtained virus in supernatant, after verification by Coomassie brilliant blue staining and Western blot, to infect the suspended HighFive cells for protein expression, harvest the proteins in supernatant and purify the target protein (Coomassie brilliant blue staining of the purified protein is as shown in FIG. 1). The purified protein was used in the cell and animal experiments. The reagents used were all purchased from Invitrogen. The Fc-ECM1 fusion protein thus prepared (consisting of the amino acids 41-811 in SEQ ID NO.: 2) was used in the activity tests and the function tests.

Cell Purification and In Vitro Differentiation $CD4^+$ T cells and $CD11c^+$ DC cells were obtained by magnetic cell sorting (Miltenyi Biotec). The purity of positive cells was above 95%. T cells were cultured in the T cell in vitro differentiation system in RPMI 1640 medium supplemented with 10% fetal calf serum (GIBCO), glutamine (2 mM), β-ME (50 mM), penicillin (50 unit/ml), streptomycin (50 mg/ml), sodium pyruvate (1 mM) and Hepes (100 mM).

The T cells were stimulated using 5 μg/ml coated anti-CD3 and 2 μg/ml soluble anti-CD28, and induced to differentiate toward different directions in the following inductive environments:

Th0-------50 U/ml IL-2, 10 μg/ml anti-IFN-γ and 10 μg/ml anti-IL-4;

Th1------10 ng/ml IL-12, 10 μg/ml anti-IL-4 and 50 U/ml IL-2;

Th17------1 ng/ml TGF-β1, 20 ng/ml IL-6, 10 ng/ml IL-1α, 10 ng/ml IL-23, 10 μg/ml anti-IFN-γ and 10 μg/ml anti-IL-4.

As appropriate for the experiment, 20 μg/ml Fc-ECM1 protein or IgG as the control was added to the inductive environment (see Example 5 for details).

Matrigel Invasion Assay

To the differentiated cells obtained as said above were added the proteins as specified or GM6001 on day 3. The cells were harvested on day 4 and counted, and were ready for use in invasion assay. In the case of pathogenic Th cells, the mouse inguinal lymph nodes were isolated on day 8 after the EAE immunization, the isolated mononuclear lymphocytes were restimulated using 50 μg/ml MOG at the density of $3 \times 10^6$ cells/ml for 3 days, then counted, and were ready for use in invasion assay.

BD BioCoat™ Matrigel™ Invasion Chamber and Control Inserts were both purchased from Biosciences. The invasion assay was performed according the manufacturer's instruction. Matrigel can mimic the basal lamina in the blood-brain barrier, and the pathogenic Th cells need to cross the basal lamina to reach the focus, while Control Inserts does not have the Matrigel layer, and the cells can directly perforate.

Briefly, the process of cell invasion assay was as follows: The Matrigel wells were provided in a 24-well plate; the plate was hydrated for 2 h in serum-free RPMI1640 in incubator at 37° C. to regenerate; RPMI1640 was then carefully removed. The Cells were all resuspended in serum-free RPMI1640 at $1\times10^6$/ml, to which were added the different proteins or the inhibitors as specified. 500 µl cell was added to the upper chamber of a Matrigel well, and 500 µl RPMI1640 supplemented with 5% serum to the lower chamber. Control Inserts, was loaded in the same way. After 22 h at 37° C. in incubator, the cells that have migrated into the lower chamber were collected and counted. Cell migration rate was calculated as the ratio between the experiment group and the control group, i.e., migration rate=the number of migrating cells in the wells of Invasion Chamber/the number of migrating cells in the wells of Control Inserts× 100%.

Preparation of Mouse CNS Monocyte Suspension

A. The experiment mice were anesthetized, chest opened, and spinal cord taken out after heart infusion of PBS.

B. The obtained bone marrow was placed on a 70 µm cell mesh, gently ground using a syringe's plunger, and the obtained tissue homogenate was washed by PBS and collected.

C. After centrifugation at 2000 rpm for 5 min, supernatant was discarded, and the tissue mass was resuspended to homogenous in 7 ml of 30% Percoll (Sigma), to which 4 ml of 70% Percoll fluid was slowly added to the bottom of the tissue suspension (using a pipette reaching to the botton of the eppendorff), centrifuged at 2000 rpm for 22 min.

D. Monocytes between the layer of 70% and the layer of 30% Percoll were collected, washed once with RPMI1640 medium containing 2% FBS, and then resuspended in an appropriate amount of medium and counted, which were then ready for use.

Flow Cytometry

To detect the ratio of the CD4$^+$ T cells that infiltrate the CNS monocytes, PE-labeled anti-mouse CD4 antibody was used for staining. The cells were analyzed using FACSCalibur Flow Cytometer (BD Biosciences).

ELISA Test

To detect the cytokine concentration in the supernatant of cell culture, IL-17 and IFN-γ ELISA dual kit purchased from R&D Systems and was used according to the manufacturer's instruction.

$^3$H Proliferation Assay

The anti-CD3 antibodies were dissolved at 1 µg/ml in PBS, and the 96-well plate was coated at 60 µg/well, let stand at 4° C. overnight. The supernatant in each well was cleared out prior to cell seeding. The purified CD4$^+$ T cells were stimulated using the anti-CD3 antibody in the pre-coated 96-well plate, where in each well was seeded with $2\times10^5$ cells and added 200 µl medium for incubation. After 60 h of growth, 1 µCi [$^3$H] thymine was added to each well, and another 12 h later. Incorporation of [$^3$H] thymine was detected to determine the status of cell proliferation. Each sample was analyzed in triplicate. At the end of culture, the cells were collected by cell collector and the amount of [$^3$H] thymine incorporation was measured with scintillation counter.

Figure 2:
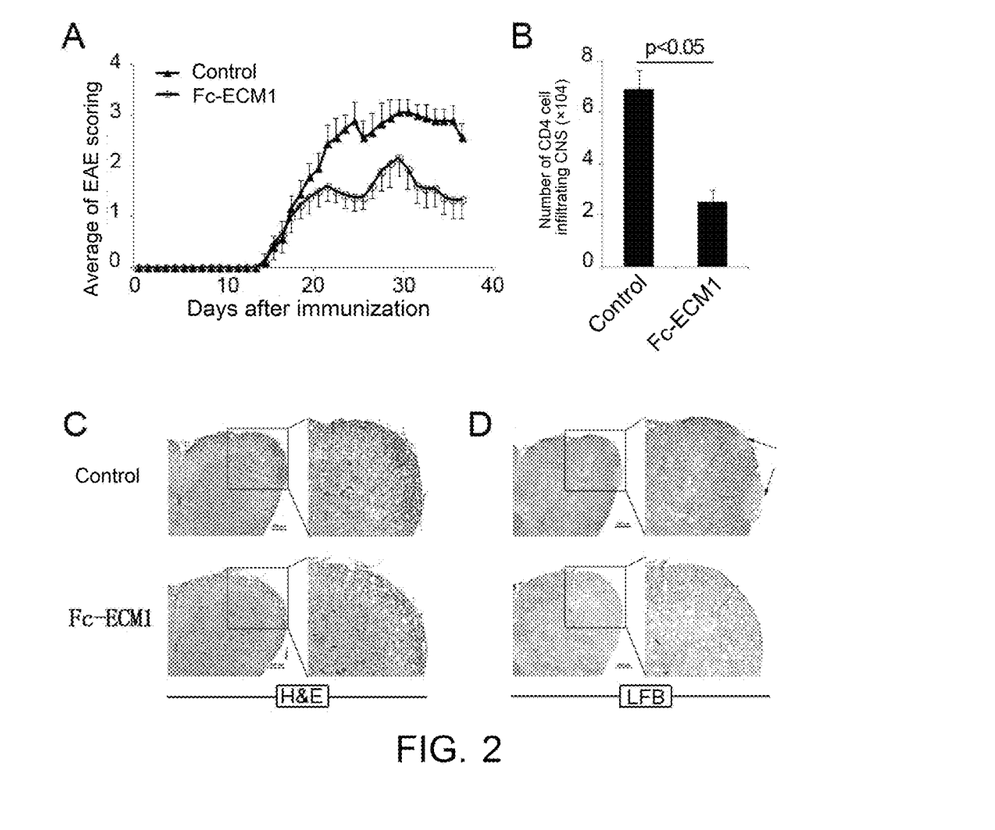
FIG. 2 demonstrates that the administration of Fc-ECM1 at middle to late stage in the mouse EAE model ihibitits progression of EAE.

II. Example 1: Fc-ECM1 treatment at a late stage effectively alleviates EAE symptom in EAE mouse model Induced EAE model was built in 6-8 week-old C57BL/6 female mice. The animals were randomly divided into groups of 9, subcutaneously immunized with MOG$_{35-55}$ on day 0, intraperitoneally injected by PTX on day 0 and day 2, as detailed in the "Establishment of EAE model and administration" above. The mice were administered with Fc-ECM1 protein at the designated time points. The C57 mice receiving EAE immunization with MOG$_{35-55}$ antigen were evenly divided into 2 experiment groups, and were respectively administered with the Fc-ECM1 protein and IgG protein as the control by tail vein injection on day 8, day 11 and day 14 (at the dosage of 100 µg/mouse). Clinical scoring was performed every day to study the effect of the Fc-ECM1 protein on EAE. According to EAE scores as shown in FIG. 2A, the severity of EAE disease in the Fc-ECM1 protein treatment group was significantly lower than the control group. Statistical difference between the scores of the groups appeared since day 21 (p<0.05).

On day 24 after the immunization, spinal cord was collected from the differentially treated EAE mice. Mononuclear cells were isolated using Percoll, counted and then surface labeled with PE-anti-CD4 antibody. The CD4$^+$ T cell ratio was detected by FACS, and the number of CD4$^+$ T cells calculated. As shown in FIG. 2B, the CD4 cells infiltrating CNS were significantly decreased by the Fc-ECM1 treatment. FIGS. 2C and D show the pathological section staining of the diseased mice collected on day 24 after the immunization. FIG. 2C shows the HE staining, which indicates that inflammatory cells infiltrating CNS decreased in the Fc-ECM1 treatment group, and FIG. 2D shows the Luxol Fast blue staining, which indicates that demyelination in the Fc-ECM1 treatment group was significantly less than that in the control group (the arrow in the figure points to indicate the position of demyelination). In generally, according to FIG. 2, at the stage where can be found the pathogenic T cell migration toward CNS in the EAE model, the Fc-ECM1 treatment can significantly alleviate the disease. Characterization of said stage of said migration can be found in documents, e.g., "EMMPRIN: A Novel Regulator of Leukocyte Transmigration into the CNS in Multiple Sclerosis and Experimental Autoimmune Encephalomyelitis", *The Journal of Neuroscience*, Jan. 12, 2011 ● 31(2):669-677.

III. Example 2: Fc-ECM1 protein treatment at an early stage can effectively alleviate morbidity in EAE Induced EAE model was built in 6-8 week-old C57BL/6 female mice. The animals were randomly divided into groups of 9. EAE was induced as described in "Establishment of EAE model and administration" above. The mice were administered with the Fc-ECM1 protein by tail vein injection on day 1, day 3, day 5 and day 7 after the EAE induction (at the dosage of 100 µg/mouse). The mice were treated with human IgG protein in the negative control group. On day 8 after the immunization, spleen and lymph node cells were isolated from 2 mice in each group. The cells were restimulated with MOG$_{35-55}$+IL-23 for 72 h in vitro. The culture supernatant of the restimulated cells was collected, the levels of secreted IFN-γ and IL-17 were detected, and at the same time, pathogenic CD4$^+$ T cell proliferation in the different groups was determined according to the [$^3$H] proliferation assay said above. The other EAE mice (7 in each group) were observed and scored for EAE mobidity. When the disease reached the peak state (day 21 after the immunization), spinal cord tissue was sampled and prepared by 4% PFA fixation, paraffin section, Luxol Fast Blue staining and H&E staining, and then, pathological damage and inflammatory cell infiltration in spinal cord tissue were detected.

Figure 3:
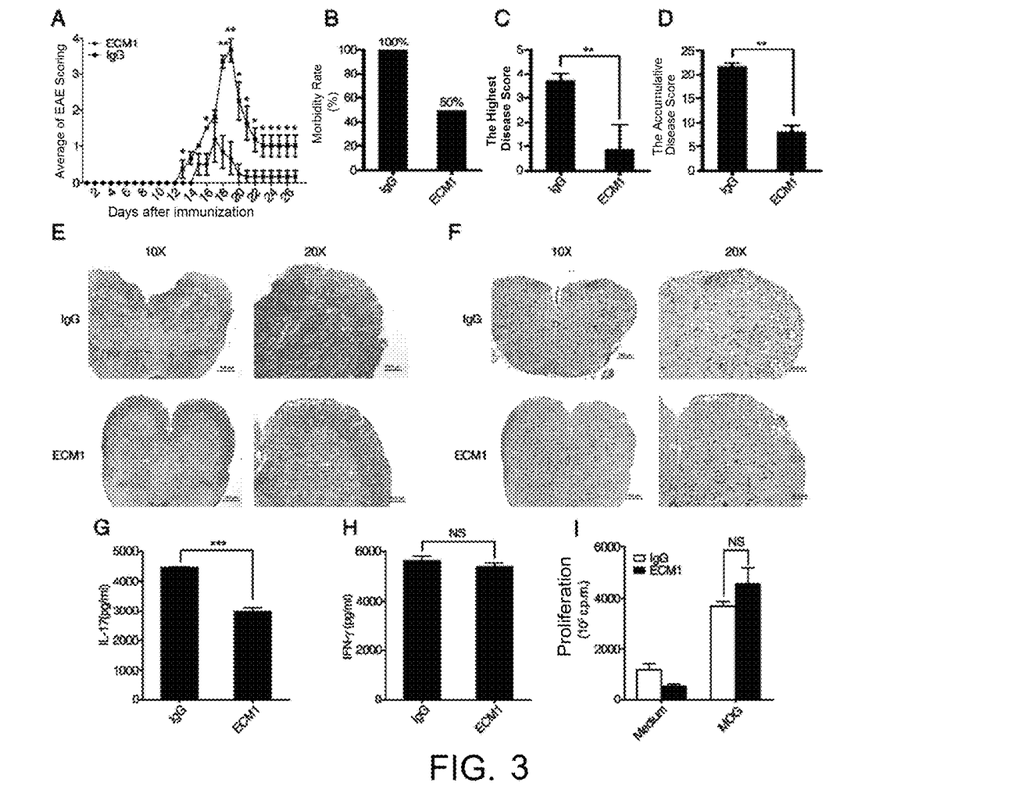
FIG. 3 demonstrates that an early treatment with Fc-ECM1 effectively prevents and alleviates EAE disease in mouse EAE model.

The results are shown in FIG. 3. FIG. 3A shows the disease scoring among EAE mice, which clearly demonstrates that compared with the negative control group treated with human IgG protein, the Fc-ECM1 protein treatment obtained a notable improvement in terms of EAE morbidity and EAE disease score. Particularly, the Fc-ECM1 treatment significantly decreased the morbidity rate of EAE (see FIG. 3B), the peak and the accumulative disease scores in the Fc-ECM1 treatment group were significantly lower than those of the control group (see FIGS. 3C and 3D). FIGS. 3E and 3F show the Luxol Fast Blue and the H&E staining of EAE mouse spinal cord tissue, respectively. As shown, compared with the IgG control group, tissue damage and inflammatory cell infiltration in spinal cord in the ECM1 treatment group were significantly reduced. On day 8 after the EAE immunization, lymph node cells were restimulated with $MOG_{35-55}$+IL-23 for 72 h in vitro, levels of secreted IL-17 (FIG. 3G) and IFN-γ (FIG. 3H) and change in proliferation (FIG. 3I) in the differentially treated group were detected. As shown, compared with the control group, IL-17 level was significantly reduced in the treatment group, IFN-γ levels were substantially even, and the ECM1 treatment had no effect on lymphocyte proliferation in EAE mice.

IV. Example 3: Fc-ECM1 inhibits T cell migration

Figure 4:
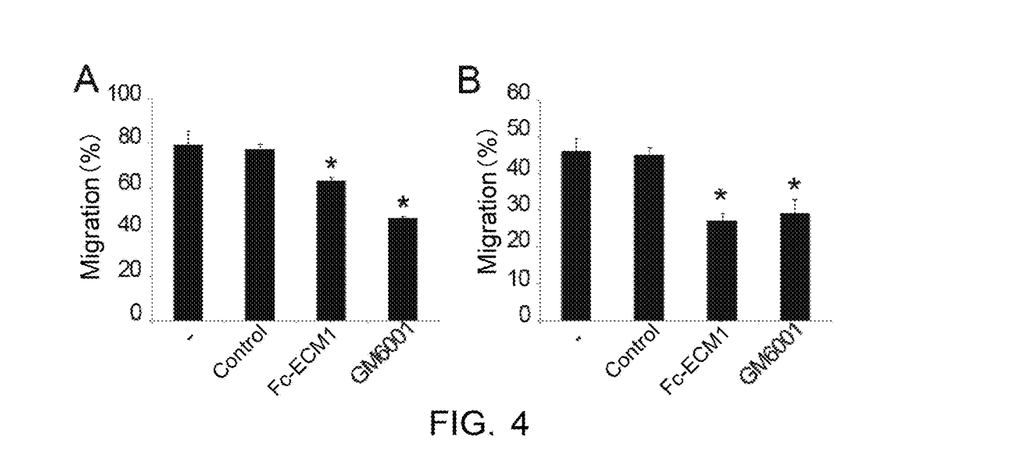
FIG. 4 demonstrates that Fc-ECM1 inhibits T cell migration.

The inventors studied the effect of the Fc-ECM1 protein on Th cell migration. Matrigel can mimic the basal lamina in the blood-brain barrier, and the Th cells need to cross the basal lamina to reach the focus. The Matrigel Invasion Assay was used to detect the migration potential of Th cells. Mouse CD4$^+$ T cells were isolated and activated with 5 μg/ml coated anti-CD3 and 2 μg/ml soluble anti-CD28 to mature. On day 3 of the Th cell culturing, the groups were respectively subject non-treatment, addition of human IgG as the control, the Fc-ECM1 protein and GM6001, and cells on day 4 of the culturing were analyzed using Matrigel Invasion Assay. As shown by the Matrigel Invasion Assay, the Fc-ECM1 protein has an inhibitory effect on Th cell migration (FIG. 4A, *: $p<0.05$).

In view that the Fc-ECM1 protein was shown as can inhibit Th cell migration in vitro, the inventors further studied the protein's effect on pathogenic T cell migration using the Matrigel Invasion Assay. Mouse inguinal lymph node cells were collected on day 8 after the EAE immunization, and the cells restimulated with MOG for 3 days were used in the cell migration experiment. In consistency with the in vitro results, in this Matrigel Invasion Assay including the corresponding treatment of IgG as the control, the Fc-ECM1 and the GM6001, ECM1 significantly inhibited pathogenic T cell migration, to a ratio comparable to GM6001 (FIG. 4B, *: $p<0.05$). Referring to FIG. 2B, which shows a reduction of CD4 cells infiltration into CNS by the Fc-ECM1 treatment, these suggested that the therapeutic action of Fc-ECM1 on EAE may be attributable to its capability of inhibiting pathogenic CD4 cells from passing the blood brain barrier and migrating into the central nervous system.

Figure 5:
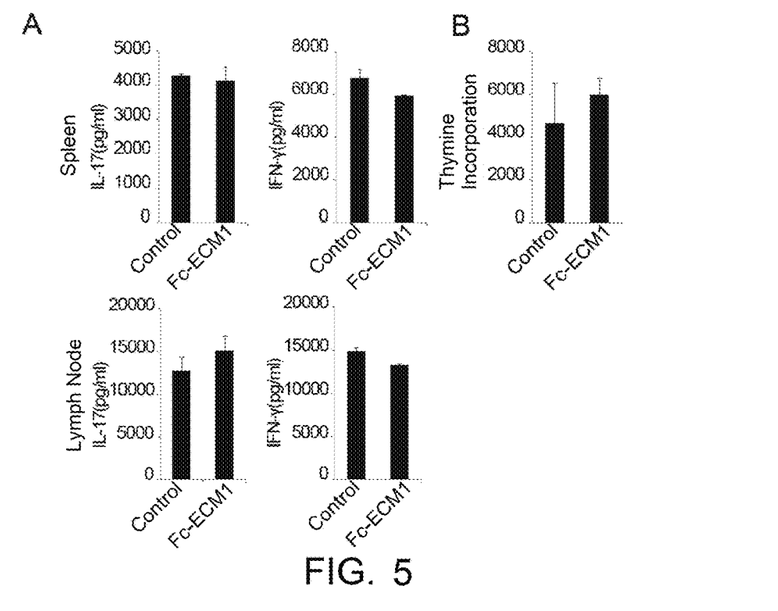
FIG. 5 demonstrates that Fc-ECM1 doesn't affect immune response level of peripheral lymphoid organ.

V. Example 4: Fc-ECM1 protein treatment at a Late stage does not affect immune response and cell proliferation in peripheral lymphoid organs The factor analysis of EAE mainly focuses on two aspects, one is the generation of antigen-specific pathogenic T cells, and the other is pathogenic T cell migration to CNS system. The inventors have for the first time determined the immune response level of peripheral lymphoid organs under the condition of EAE immunization and protein treatment as described in Example 3. Mouse spleen and lymph nodes were collected on day 15 of the immunization, monocytes were isolated and restimulated with 50 μg/ml MOG for 3 days, and then cytokine secretion in the supernatant was detected. As shown in FIG. 5A, both in spleen and in lymph nodes, after the MOG in vitro restimulation, there were no obvious difference in terms of IL-17 and IFNg expression between the Fc-ECM1 treatment group and the control group.

At the same time, the inventors have also determined mouse spleen cell proliferation after MOG restimulation in the two groups using the $^3$H incorporation method. As described above, monocytes were isolated, restimulated with MOG for 60 h before adding [$^3$H] thymine. The incorporation of [$^3$H] thymine at 72 h was determined. Again, no obvious difference between the groups was observed (FIG. 5B). This suggests that the Fc-ECM1 protein does not affect the generation of peripheral pathogenic T cells in an EAE disease model.

Figure 6:
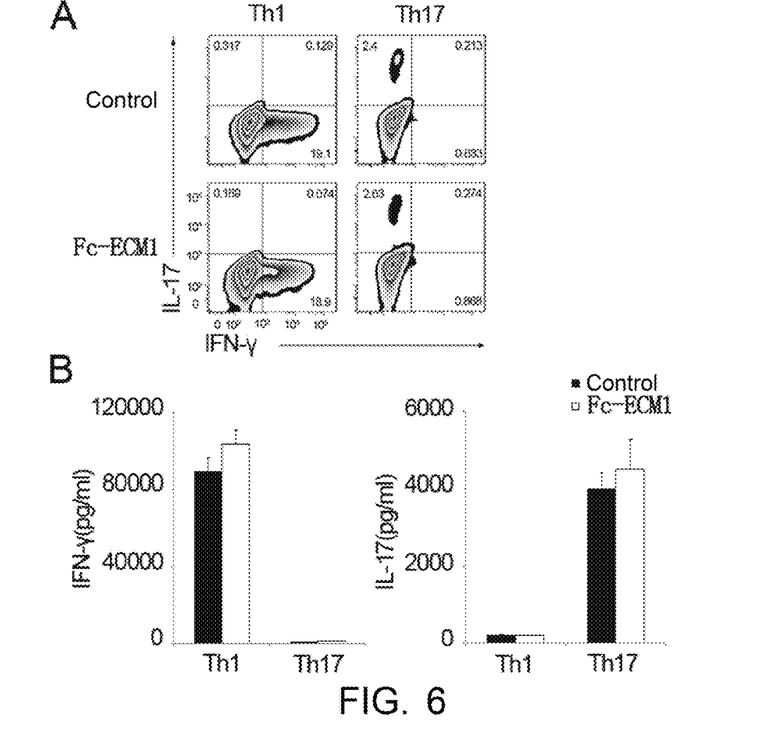
FIG. 6 demonstrates that Fc-ECM1 protein doesn't affect differentiation and proliferation of Th17 cell in vitro.

VI. Example 5: Fc-ECM1 protein does not directly affect the In Vitro differentiation of Th1 and Th17 cells It is now believed that Th1 and Th17 cells are the major pathogenic Th cells. Thus, the inventors studied the effect of the Fc-ECM1 protein on differentiation of CD4$^+$ T cell in the Th1 and the Th17 systems in vitro. Mouse CD4$^+$ T cells were obtained by immunomagnetic separation, cultured under the conditions respectively appropriate for the Th1 and the Th17 differentiation, and the Fc-ECM1 protein or the control protein were added to the culture systems. After 4-days of differentiation, the cells were harvested and intracellularly stained for flow cytometry. The supernatant was analyzed by ELISA. IFN-γ and IL-17 are recognized fingerprint cytokines respectively designated for Th1 cells and Th17 cells. The FACS (FIG. 6A) and the ELISA (FIG. 6B) both showed that Fc-ECM1 protein didn't affect the differentiation of Th1 and Th17 cells in vitro.

VII. Example 6: Fc-ECM1 protein inhibits formation of pathogenic Th17 cells and is therapeutically effective Generation and migration of pathogenic T cells are two key steps in EAE development, wherein pathogenic T cells are generally developed and formed at an early stage of EAE immunity (no later than 7 days after the immunization), and therefore, it is speculated that pathogenic T cell migration may have some effect in the development of EAE. To eliminate the effect, 6-8 week-old C57BL/6 female mice were used to build the induced EAE model as described in "Establishment of EAE model and administration". The Fc-ECM1 and IgG were administered via tail vein injection on day 1, day 3, day 5 and day 7 after the immunization (100 μg/mouse). On day 8 after the immunization, spleen cells were isolated, restimulated by $MOG_{35-55}$+IL-23 (5 μg/ml MOG+10 ng/ml IL-23) in vitro, before adoptive-transferred to C57 recipient female mice at 1×10$^7$ cells/mouse, wherein the mice had received a half lethal dosage of radiation. The recipient mice were then observed for EAE mobidity.

Figure 7:
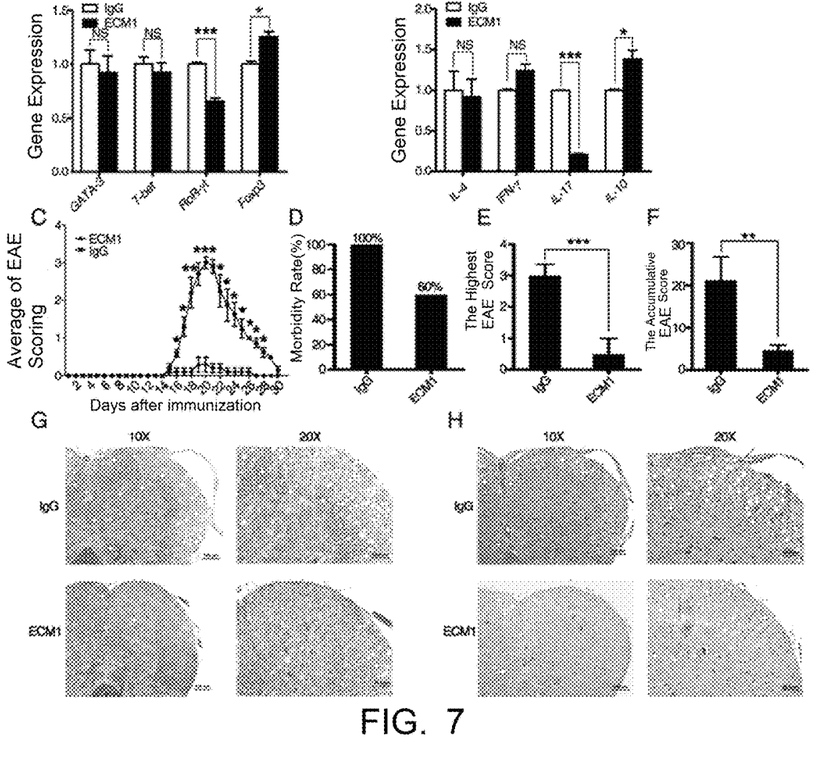
FIG. 7 demonstrates that Fc-ECM1 protein inhibits the formation of pathogenic Th17 cell and exhibits a therapeutic effect.

As shown in FIG. 7, a early-stage tail vein injection of Fc-ECM1 protein before the adoptive transfer reduced the mobidity of EAE. The inventors compared spleen cells of the EAE mice respectively receiving the Fc-ECM1 protein treatment and the IgG treatment. The expression levels of critical transcription factors in different sub-populations of Th cell and the cytokines respectively specific for each of the sub-populations in the recipient mice are shown in FIGS. 7A and 7B. As seen, compared with IgG treatment, in recipient mice transferred with CD4$^+$ T cell from the EAE mice treated with the Fc-ECM1 protein, expression levels of the critical transcription factor RoRγt and the fingerprint cytokine IL-17 of Th17 cells declined sharply, suggesting that the Th17 differentiation was strongly inhibited in vivo. Correspondingly, EAE disease scoring in recipient mice transferred with cells from different treatment groups showed that, the disease score in the recipient mice transferred with the cells from the Fc-ECM1 treated group was significantly lower than that in the recipient mice transferred with the cells from the control human IgG treated group (FIG. 7C). The statistics of EAE morbidity rate (FIG. 7D), the highest EAE disease score (FIG. 7E) and the accumulated EAE disease score (FIG. 7F) in the EAE recipient mice receiving the adoptive transfer all showed that, the ECM1 protein treatment can significantly reduce pathogenicity of EAE pathogenic T cells. The results of Luxol Fast Blue staining and H&E staining of mouse spinal cord tissue section showed that, damage in the spinal cord tissue (FIG. 7G) and number of the infiltrated inflammatory cells in CNS (FIG. 7H) both significantly decreased in the recipient mouse, after being transferred with the cells from the mice treated by the ECM1 protein.

VIII. Example 7: Fc-ECM1 inhibits activation of pre-TGF-β and in turn affects Th17 cell differentiation To study why the Fc-ECM1 protein didn't directly affect the Th17 cell differentiation in vitro while strongly inhibited Th17 cell differentiation in vivo, we induced Th1 and Th17 differentiation under the condition of anti-CD3 and anti-CD28 antibody activation in vitro, wherein the Fc-ECM1 protein and the IgG protein (as control) were added to the culture systems, separately. The flow cytometry results the Th1 and the Th17 differentiation showed that, in the absence of antigen presenting cell (e.g., DC cell), addition of the foreign Fc-ECM1 protein didn't affect the Th17 and the Th1 cell differentiation in vitro (supra). Meanwhile, the ELISA assay on IFN-γ and on IL-17 secretion levels of the Th1 and the Th17 cells showed that, generation of the Th1 cell-specific and the Th17 cell-specific cytokines were not affected. These results were in consistent with what was observed in Example 5 (supra).

Figure 8:
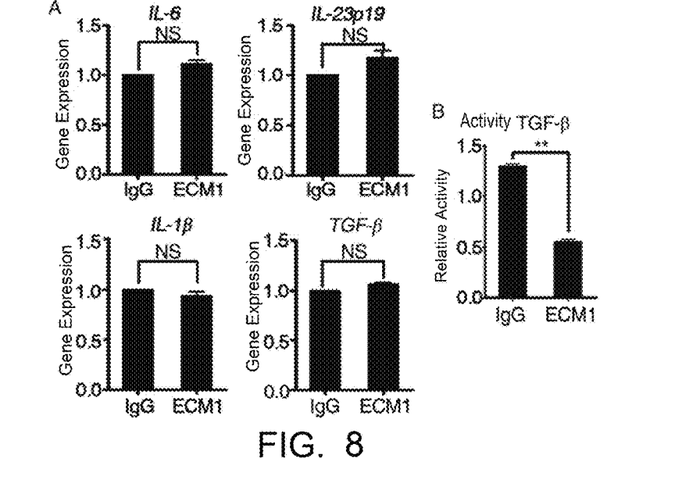
FIG. 8 demonstrates that Fc-ECM1 inhibits the activation of pre-TGF-β and in turn affects Th17 cell differentiation.

With the knowledge that TGF-β is initially expressed within the cells as an inactive precursor and then being secreted into the outside of the cells, before turning into a bioactive TGF-β by the extracellular cleavage and activation, we assayed the active TGF-β level in the supernatant of a DC cell culture ($1 \times 10^6$/well in a 24-well plate, RPMI1640+10% FBS) with the addition of the Fc-ECM1 protein (4 μg/ml). The results showed that, although adding Fc-ECM1 protein didn't affect the TGF-β mRNA expression in DC cells (see the result of gene expression shown in FIG. 8A), it inhibited the activation of latent-TGF-β by DC cells. Compared with the control group in which equivalent amount of IgG was added, after adding, the level of active TGF-β in the supernatant of DC cell culture containing Fc-ECM1 was significantly lower (as shown in FIG. 8B, TGF-β activity determined by the luciferase assay in the supernatant of DC cell culture)

IX. Example 8: The interaction between Fc-ECM1 and integrin αv inhibits activation of latent-TGF-β and Th17 cell differentiation The inventors also identified the molecules that can interact with the Fc-ECM1 protein in T cells using the protein mass spectrometry, for studying the regulatory effect of Fc-ECM1 on TGF-β activation in DC cells. The results of protein mass spectrometry showed that there was interaction between Fc-ECM1 and integrin αv in T cells.

Figure 9:
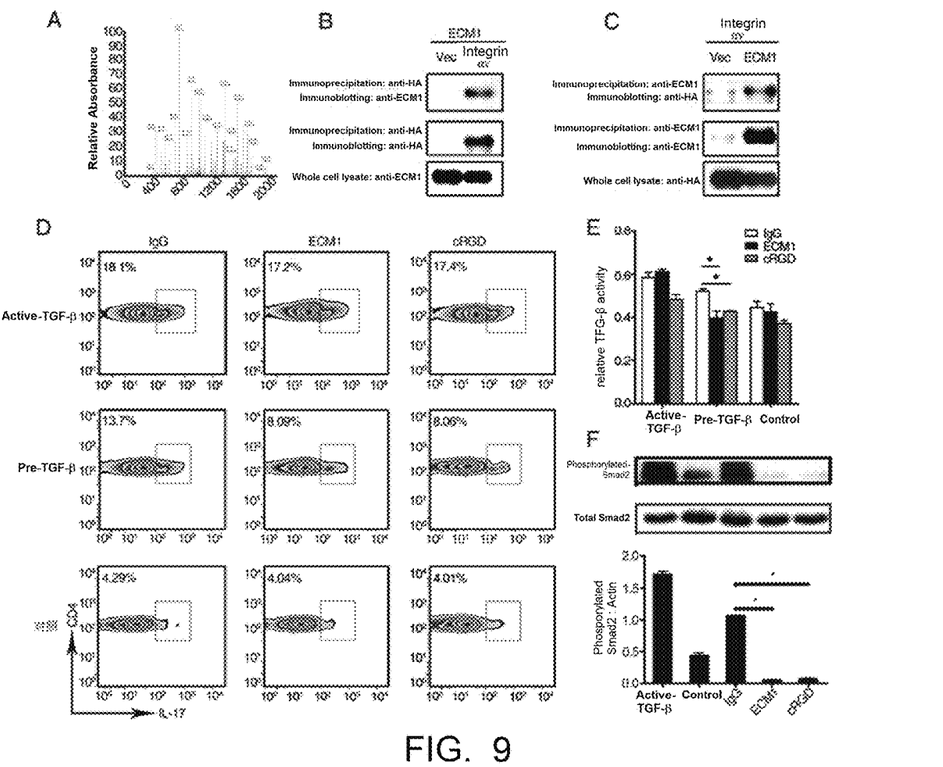
FIG. 9 demonstrates that the interaction between Fc-ECM1 and integrin αv inhibits the activation of pre-TGF-β and Th17 cell differentiation.

We cloned and constructed an expression plasmid of integrin αv to testify the results of mass spectrometry. The results of co-immunoprecipitation (CoIP) in vitro showed that there was a strong interaction between Fc-ECM1 and integrin αv in vitro (FIGS. 9B and 9C). To assay whether this interaction affects the activation of latent-TGF-β by integrin αv and the subsequent Th17 cell differentiation, we cultured the DC cells and the CD4$^+$ T cells isolated from mouse spleen in the presence of latent-TGF-β in vitro, adding Fc-ECM1 at the same time, and using human IgG as the negative contro and cRGD as the positive control. After co-culturing in vitro for three days, the supernatant was collected, and the levels of IL-17 and active TGF-β in the supernatant were determined. Th17 cell differentiation ratio was detected by flow cytometry staining. Results showed that: Fc-ECM1 significantly inhibited Th17 differentiation in the co-culture system (FIG. 9D), and also the level of active TGF-β (FIG. 9E) in the supernatant.

It was known that once the TGF-β signaling pathway is activated, Smad2 is first phosphorylated, followed by the subsequent steps of signaling. There have been reported that A549 cells express integrin αv and comprise the TGF-β signaling pathway. Thus, we used A549 cells to assay the impact of Fc-ECM1 on the intracellular Smad2 phosphorylation by Western Blot, to determine whether Fc-ECM1 inhibits the activation of TGF-β signaling. Results showed that, compared with the negative control group of IgG, Fc-ECM1 significantly inhibited intracellular Smad2 phosphorylation, which was comparable to the result obtained with the positive control of cRGD. This demonstrated that Fc-ECM1 can inhibit the activation of TGF-β signaling, thus reduces Smad2 phosphorylation.

X. Example 9: Fc-ECM1 transgenic mice are protected against EAE induction

To determine whether the endogenous ECM1 protein also has therapeutical effect, the inventors induced EAE in ECM1 transgenic mice (ECM1$^{Tg}$) with ECM1-over expressing T cells. Lymph node cells were isolated on day 8 after the EAE immunization, restimulated with MOG$_{35-55}$+IL-23 in vitro and assayed on cytokine secretion levels. The mice were scored for EAE mobidity and analyzed on pathology.

Figure 10:
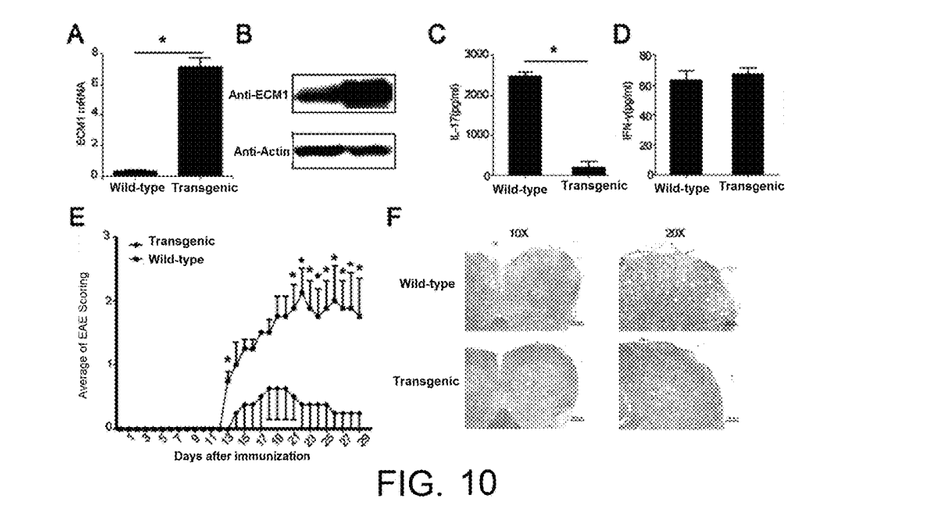
FIG. 10 demonstrates the protection against EAE induction in an ECM1 transgenic mouse.

First, we determined the transgene effects in the ECM1 transgenic mice by real time PCR and Western Blot, the results being shown in FIGS. 10A and 10B, respectively. Compared with the wild-type mice, in the transgenic mice, the expression of ECM1 in CD4$^+$ T cells was high at both the mRNA level and the protein level. The ELISA assay after in vitro restimulation showed that, compared with wild-type mice, in ECM1 transgenic mice, the IL-17 secretion in lymph node cells was significantly reduced (FIG. 10C), while the production of IFN-γ was not changed (FIG. 10E). Luxol Fast Blue staining of the corresponding spinal cord tissue showed that pathological damage in the spinal cord tissue in the ECM1 transgenic mice was significantly less than that of wild-type mice (FIG. 10F). Therefore, as shown by these results, both exogenous Fc-ECM1 recombinant protein and endogenous ECM1 have therapeutical effect on EAE.

In the above, in way of specific examples, are illustrated the cloning, expression and purification of Fc-ECM1 and its use in treating multiple sclerosis. It should be understood that, these examples are merely provided for the purpose of illustration, rather than limitation on the scope of the invention. Based on the present disclosure, modifications, changes, variations and other equivalent embodiments of the invention, particularly the physiologically active protein of the invention, would be obvious to those skilled in the art as and are thus encompassed by the scope of the invention.

REFERENCES

All the references as cited are incorporated herein by reference in their entirety for all purposes.

1. Compston, A., and Coles, A. (2008). Multiple sclerosis. *Lancet* 372, 1502-1517.

2. Gasperini, C., and Ruggieri, S. (2012). Development of oral agent in the treatment of multiple sclerosis: how the first available oral therapy, fingolimod will change therapeutic paradigm approach. *Drug Des Devel Ther* 6, 175-186.
3. Bhalerao, J., P. Tylzanowski, J. D. Filie, C. A. Kozak, and J. Merregaert. (1995). Molecular cloning, characterization, and genetic mapping of the cDNA coding for a novel secretory protein of mouse. Demonstration of alternative splicing in skin and cartilage. *The Journal of biological chemistry* 270:16385-16394.
4. Mongiat, M., J. Fu, R. Oldershaw, R. Greenhalgh, A. M. Gown, and R. V. Iozzo. (2003). Perlecan protein core interacts with extracellular matrix protein 1 (ECM1), a glycoprotein involved in bone formation and angiogenesis. *The Journal of biological chemistry* 278:17491-17499.
5. Smits, P., Y. Poumay, M. Karperien, P. Tylzanowski, J. Wauters, D. Huylebroeck, M. Ponec, and J. Merregaert. (2000). Differentiation-dependent alternative splicing and expression of the extracellular matrix protein 1 gene in human keratinocytes. *The Journal of investigative dermatology* 114:718-724.
6. Chan, I. (2004). The role of extracellular matrix protein 1 in human skin. *Clinical and experimental dermatology* 29:52-56.
7. Clegg A, Bryant J. (2001), Immunomodulatory drugs for multiple sclerosis: a systematic review of clinical and cost effectiveness. *Expert Opin Pharmacother* 2: 623-639.
8. Prendergast C. and Anderton S. (2009). Immune Cell Entry to Central Nervous System—Current Understanding and Prospective Therapeutic Targets. *Endocrine, Metabolic & Immune Disorders—Drug Targets* 9:315-327
9. Engelhardt B. (2008), Immune cell entry into the central nervous system: Involvement of adhesion molecules and chemokines. *J Neurol Sci* 274: 23-26

What claimed is:

1. A fusion protein wherein the fusion protein comprises amino acid residues 41-580 in SEQ ID NO: 2 and a Fc sequence comprising amino acid residues 583-811 in SEQ ID NO.: 2.

2. A pharmaceutical composition comprising: (A) a therapeutically effective amount of the fusion protein according to claim 1; and (B) a pharmaceutically acceptable carrier or excipient.

3. The pharmaceutical composition according to claim 2, wherein the pharmaceutical composition comprises 0.001-99.9 wt % of the fusion protein, based on the total weight of the pharmaceutical composition.

4. The pharmaceutical composition according to claim 2, wherein the carrier is selected from the group consisting of water, an aqueous buffer, ethanol, a polyol, vegetable oil, an injectable organic ester, and a mixture of two or more of the above.

5. A medicament for treating or alleviating one or more symptom(s) of multiple sclerosis, wherein the medicament comprises the fusion protein according to claim 1.

6. The medicament according to claim 5, wherein the medicament comprises: (A) a therapeutically effective amount of the fusion protein; and (B) a pharmaceutically acceptable carrier.

7. The medicament according to claim 5, wherein the medicament is formulated for oral administration, injection, local administration; and/or wherein the medicament is formulated in a unit dosage form.

8. A fusion protein comprising an extracellular matrix protein 1 and an Fc sequence of IgG, wherein the fusion protein comprises an amino acid sequence as set forth by residues 41-811 in SEQ ID NO.: 2.

9. The medicament according to claim 7, wherein the injection is subcutaneous injection, intravenous injection, intraperitoneal, intramuscular injection, intrasternal injection, or infusion.

10. The pharmaceutical composition according to claim 4, wherein the aqueous buffer is selected from the group consisting of phosphate buffer, Tris buffer, borate buffer, succinate buffer, histidine buffer, citrate buffer and a mixture of two or more of the above.

11. The pharmaceutical composition according to claim 4, wherein, the polyol is selected from the group consisting of glycerol, propanediol, polyethylene glycol, and a mixture of two or more of the above; and/or wherein, the vegetable oil is olive oil; and/or wherein, the injectable organic ester is ethyl oleate.

* * * * *